(12) United States Patent
Kato (10) Patent No.: US 8,508,725 B2
(45) Date of Patent: Aug. 13, 2013

(54) REFRACTIVE INDEX DISTRIBUTION MEASURING METHOD AND APPARATUS USING POSITION MEASUREMENT AND A REFERENCE OBJECT

(75) Inventor: Seima Kato, Utsunomiya (JP)

(73) Assignee: Canon Kabushiki Kaisha (JP)

(*) Notice: Subject to any disclaimer, the term of this patent is extended or adjusted under 35 U.S.C. 154(b) by 112 days.

(21) Appl. No.: 12/917,521

(22) Filed: Nov. 2, 2010

(65) Prior Publication Data

US 2011/0134438 A1 Jun. 9, 2011

(30) Foreign Application Priority Data

Dec. 7, 2009 (JP) ................................ 2009-277496

(51) Int. Cl.
*G01N 21/41* (2006.01)
(52) U.S. Cl.
USPC ........................... 356/128; 356/124; 356/517
(58) Field of Classification Search
USPC .................. 356/124–128, 517–518, 73.1, 30, 356/31
See application file for complete search history.

(56) References Cited

U.S. PATENT DOCUMENTS

| | | | |
|---|---|---|---|
| 4,265,534 A | | 5/1981 | Remijan |
| 4,541,697 A | | 9/1985 | Remijan |
| 4,542,989 A | | 9/1985 | Remijan |
| 4,565,449 A | * | 1/1986 | Grego ............................ 356/484 |
| 4,744,654 A | | 5/1988 | Jinno et al. |
| 4,934,818 A | | 6/1990 | Glantschnig et al. |
| 5,151,752 A | | 9/1992 | Oono et al. |
| 5,309,214 A | | 5/1994 | Hashimoto |
| 5,526,118 A | * | 6/1996 | Miyagawa et al. ............ 356/484 |
| 6,765,661 B2 | * | 7/2004 | Biel et al. ........................ 356/124 |
| 7,388,676 B2 | | 6/2008 | Sawada |
| 2006/0159332 A1 | | 7/2006 | Sawada |
| 2007/0109555 A1 | * | 5/2007 | Gustafsson et al. ........... 356/517 |
| 2009/0109401 A1 | * | 4/2009 | Van Heugten ................. 351/221 |

(Continued)

FOREIGN PATENT DOCUMENTS

| | | |
|---|---|---|
| JP | 58-045526 A | 3/1983 |
| JP | 61-070436 A | 4/1986 |

(Continued)

OTHER PUBLICATIONS

KR Office Action issued Aug. 10, 2012 for KR10-2009-0120318.

(Continued)

*Primary Examiner* — Tarifur Chowdhury
*Assistant Examiner* — Michael P LaPage
(74) *Attorney, Agent, or Firm* — Rossi, Kimms & McDowell LLP (57) ABSTRACT

The measuring method includes a step of causing reference light to enter an object placed in a first medium to measure a first transmitted wavefront, a step of causing the reference light to enter the object placed in a second medium to measure a second transmitted wavefront, a step of measuring first and second placement positions where the object is placed in the first and second media, and a calculating step of calculating an internal refractive index distribution of the object by using measurement results of the first and second transmitted wavefronts. The calculating step calculates the internal refractive index distribution from which a shape component of the object is removed by using the measurement results of the first and second transmitted wavefronts, and first and second reference transmitted wavefronts of a reference object to be placed at positions identical to the first and second placement positions.

8 Claims, 5 Drawing Sheets

(56) References Cited

U.S. PATENT DOCUMENTS

| | | |
|---|---|---|
| 2009/0147241 A1* | 6/2009 | Shlezinger et al. .............. 356/30 |
| 2010/0165355 A1 | 7/2010 | Kato |
| 2010/0245842 A1 | 9/2010 | Kato |
| 2011/0292379 A1 | 12/2011 | Kato |
| 2012/0139136 A1 | 6/2012 | Kato |
| 2012/0241989 A1 | 9/2012 | Sugimoto |

FOREIGN PATENT DOCUMENTS

| | | |
|---|---|---|
| JP | 1-35282 B2 | 7/1989 |
| JP | 1-316627 A | 12/1989 |
| JP | 02-008726 A | 1/1990 |
| JP | 2-008726 A | 1/1990 |
| JP | 03-128411 A | 5/1991 |
| JP | 03-225259 A | 10/1991 |
| JP | 08-014852 A | 1/1996 |
| JP | 08-304229 A | 11/1996 |
| JP | 11-044641 A | 2/1999 |
| JP | 2005-106835 A | 4/2005 |
| JP | 2005-201724 A | 7/2005 |
| JP | 2006-200999 A | 8/2006 |
| JP | 2010-151578 A | 7/2010 |

OTHER PUBLICATIONS

Takeda, Mitsuo et al. "Lateral aberration measurements with a digital Talbot interferometer," Applied Optics, vol. 23, No. 11, Jun. 1, 1984, pp. 1760-1764.

Takeda, Mitsuo et al. "Fourier-transform method of fringe-pattern analysis for computer-based topography and interferometry," Optical Society of America, vol. 72, No. 1, Jan. 1982, pp. 156-160.

International Search Report issued Aug. 30, 2011 for PCT/JP2011/062041.

Ranjbar, et al., "Nondestructive Measurement of Refractive Index Profile of Optical Fiber Preforms Using Moire Technique and Phase Shift Method", Optical Communication, vol. 6025, 605250, 2006.

* cited by examiner

REFRACTIVE INDEX DISTRIBUTION MEASURING METHOD AND APPARATUS USING POSITION MEASUREMENT AND A REFERENCE OBJECT

BACKGROUND OF THE INVENTION

1. Field of the Invention

The present invention relates to a method and an apparatus for measuring a refractive index distribution of an object such as an optical element.

2. Description of the Related Art

Optical elements such as lenses that are used for optical apparatuses such as digital cameras and laser beam printers require high refractive indices. On the other hand, molding technology enables easy production of complex shapes such as aspheric surfaces even when using optical glasses and plastics having high refractive indices.

However, the molding sometimes causes, inside the optical element, refractive index nonuniformity depending on molding conditions. Such internal refractive index nonuniformity greatly affects optical characteristics of the optical element, which may make it impossible to obtain desired optical characteristics. Therefore, highly accurate measurement of internal optical homogeneity of the optical element having a high refractive index is required.

Methods of measuring the optical homogeneity generally include interferometries that measure a transmitted wavefront of an object (optical element) highly accurately processed to measure an internal refractive index distribution thereof. Moreover, a method is proposed which places an object between glass plates and soaks the object in oil being provided therebetween and having a refractive index approximately equal to that of the object to reduce surface accuracy errors of the object.

Japanese Patent Laid-Open No. 01-316627 discloses a method which measures a transmitted wavefront of an object soaked in a medium (matching oil) having a refractive index approximately equal to that of the object to obtain optical properties of the object. This method enables measurement of an internal refractive index distribution of the object without accurate processing of the object.

Japanese Patent Laid-Open No. 02-008726 discloses a method which measures a transmitted wavefront of an object soaked in a first matching oil having a refractive index approximately equal to that of the object, and further measures a transmitted wavefront of the object soaked in a second matching oil having a refractive index slightly different from that of the object. The disclosed method obtains a shape and a refractive index distribution of the object based on the transmitted wavefronts measured using the first and second matching oils.

In the measurement with the second matching oil, influences of the refractive index distribution and shape of the object appear as interference fringes on a detector for measuring the transmitted wavefront. Therefore, it is necessary that the refractive index of the second matching oil be slightly different from that of the object within a range where the interference fringes are not exceedingly dense.

The measuring methods disclosed in Japanese Patent Laid-Open Nos. 01-316627 and 02-008726 need the matching oil having the refractive index approximately equal to that of the object. However, matching oils having high refractive indices generally have low transmittances. Therefore, when measuring a transmitted wavefront of an object whose refractive index is high by the measuring methods disclosed in Japanese Patent Laid-Open Nos. 01-316627 and 02-008726, the detector outputs only a small signal, which deteriorates measurement accuracy.

SUMMARY OF THE INVENTION

The present invention provides a method and an apparatus capable of highly accurately measuring an internal refractive index distribution of a high refractive index object even when soaking the object in a low refractive index medium.

The present invention provides as one aspect thereof a refractive index distribution measuring method including a first measuring step of placing an object in a first medium having a first refractive index lower than a refractive index of the object, and of causing reference light to enter the object to measure a first transmitted wavefront of the object, a second measuring step of placing the object in a second medium having a second refractive index lower than the refractive index of the object and different from the first refractive index, and of causing the reference light to enter the object to measure a second transmitted wavefront of the object, a position measuring step of measuring a first placement position where the object is placed in the first medium and a second placement position where the object is placed in the second medium, and a calculating step of calculating an internal refractive index distribution of the object by using measurement results of the first and second transmitted wavefronts. The calculating step calculates the internal refractive index distribution from which a shape component of the object is removed by using the measurement results of the first and second transmitted wavefronts, a first reference transmitted wavefront of a reference object to be placed in the first medium at a position identical to the first placement position and a second reference transmitted wavefront of the reference object to be placed in the second medium at a position identical to the second placement position, the reference object having a shape identical to that of the object and a specific internal refractive index distribution.

The present invention provides as another aspect thereof a manufacturing method of an optical element using the above-described refractive index distribution measuring method.

The present invention provides as still another aspect thereof a refractive index distribution measurement apparatus including a transmitted wavefront measuring part configured to cause reference light to enter an object, which is placed in a first medium having a first refractive index lower than a refractive index of the object, to measure a first transmitted wavefront of the object, and cause the reference light to enter the object, which is placed in a second medium having a second refractive index lower than the refractive index of the object and different from the first refractive index, to measure a second transmitted wavefront of the object, a position measuring part configured to measure a first placement position where the object is placed in the first medium and a second placement position where the object is placed in the second medium, and a calculating part configured to calculate an internal refractive index distribution of the object by using measurement results of the first and second transmitted wavefronts. The calculating part calculates the internal refractive index distribution from which a shape component of the object is removed by using the measurement results of the first and second transmitted wavefronts, a first reference transmitted wavefront of a reference object to be placed in the first medium at a position identical to the first placement position and a second reference transmitted wavefront of the reference object to be placed in the second medium at a position identical to the second placement position, the reference object having a shape identical to that of the object and a specific internal refractive index distribution.

Other aspects of the present invention will become apparent from the following description and the attached drawings.

DESCRIPTION OF THE PREFERRED EMBODIMENTS

Exemplary embodiments of the present invention will hereinafter be described with reference to the accompanying drawings.

[Embodiment 1]

In a first embodiment (Embodiment 1) of the present invention, description will be made of a refractive index distribution measuring method that measures transmitted wavefronts of an object being soaked in two media (air and water, for example) to calculate an internal refractive index distribution of the object.

Figure 1A:
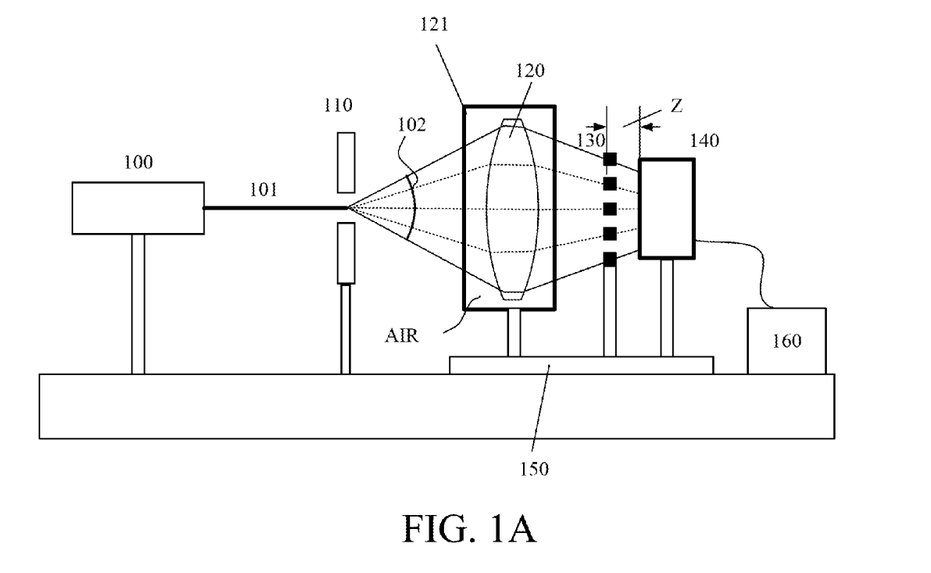
FIGS. 1A and 1B show a configuration of a refractive index distribution measuring apparatus practicing a refractive index distribution measuring method that is Embodiment 1 of the present invention.

FIG. 1A shows a configuration of a Talbot interferometer (refractive index measuring apparatus) that soaks an object 120 which is an optical element such as a lens in air (first medium) to measure a transmitted wavefront (first transmitted wavefront) of the object 120. The object 120 is placed inside an object case 121 and soaked in the air. A refractive index (first refractive index) of the air is lower than that of the object 120 by 0.01 or more.

Laser light emitted from a laser light source (for example, a He—Ne laser light source) 100 passes through a pinhole (optical member) 110 to be diffracted thereat. The laser light, that is, the diffracted light that has been diffracted by the pinhole 110 passes through the air in the object case 121, and then enters the object 120 whose object plane corresponds to the pinhole 110 as reference light 102 to be transmitted therethrough. A diameter φ of the pinhole 110 is designed to be small such that the reference light 102 can be regarded as an ideal spherical wave. Specifically, the diameter φ is designed such that an object-side numerical aperture NAO and a wavelength λ of the laser light source 100 satisfy the following condition:

$$\phi \approx \frac{\lambda}{NAO} \qquad (1)$$

For example, the diameter φ of the pinhole 110 can be set to about 2 μm in a case where the wavelength λ is 600 nm and the NAO is about 0.3.

The laser light that has been transmitted through the object 120 and the air in the object case 121 passes through an orthogonal diffraction grating 130 that is a two-dimensional diffraction grating, and then is captured (measured) by an image-pickup element 140, such as a CCD sensor or a CMOS sensor, which is a detector. The image-pickup element 140 is hereinafter referred to as the "CCD 140".

When an image-side numerical aperture of the object 120 is small, a distance Z between the diffraction grating 130 and the CCD 140 satisfying the following Talbot condition (2) generates on the CCD 140 interference fringes as a self-image of the diffraction grating 130:

$$\frac{Z_0 Z}{Z_0 - Z} = \frac{md^2}{\lambda} \qquad (2)$$

In the condition (2), the distance Z between the diffraction grating 130 and the CCD 140 is hereinafter referred to as the "Talbot distance". Moreover, m represents a natural number, and d represents a grating pitch of the diffraction grating 130. $Z_0$ represents a distance from the diffraction grating 130 to an image plane of the object 120. The grating pitch d of the diffraction grating 130 is set depending on an amount of aberration of the object 120.

The laser light source 100, the pinhole 110, the diffraction grating 130 and the CCD 140 which are constituent elements of the refractive index measuring apparatus, and the object case 121 inside which the object 120 is placed and which is also a constituent element of the refractive index measuring apparatus are movable relatively to each other while being guided by a rail 150 installed in parallel with an optical axis of the object 120. The laser light source 100, the pinhole 110, the diffraction grating 130, the CCD 140 and the object case 121 constitute a transmitted wavefront measuring device/part. The present specification also identifies structure in terms of "part. The term "part" used herein is intended to refer to structure, namely a device, mechanism, or apparatus.

Figure 1B:
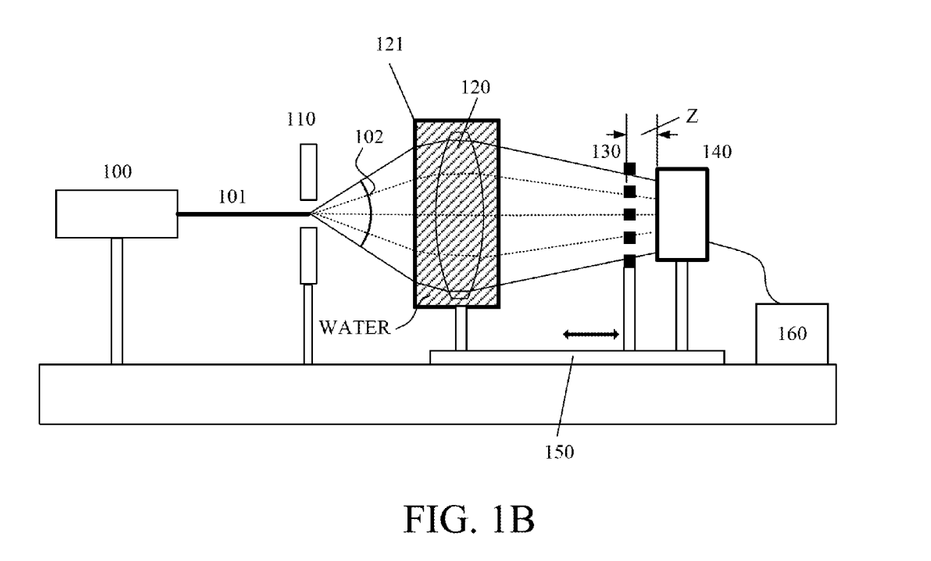

FIG. 1B shows a configuration of the Talbot interferometer that soaks the object 120 in water (second medium) to measure a transmitted wavefront (second transmitted wavefront) of the object 40. The object 120 is placed inside the object case 121 and soaked in the water. A refractive index (second refractive index) of the water is lower than that of the object 120 by 0.01 or more, and is different from that of the air.

The diffraction grating 130 and the CCD 140 are arranged at positions farther from the object 120 than that in the case of using the air as the medium as shown in FIG. 1A.

The laser light emitted from the laser light source 100 passes through the pinhole 110 to be diffracted thereat. The laser light, that is, the diffracted light (reference light) that has been diffracted by the pinhole 110 passes through the water in the object case 121, and then enters the object 120 to be transmitted therethrough. The laser light that has been transmitted through the object 120 and the water in the object case 121 passes through the diffraction grating 130, and then is captured (measured) by the CCD 140.

Figure 2:
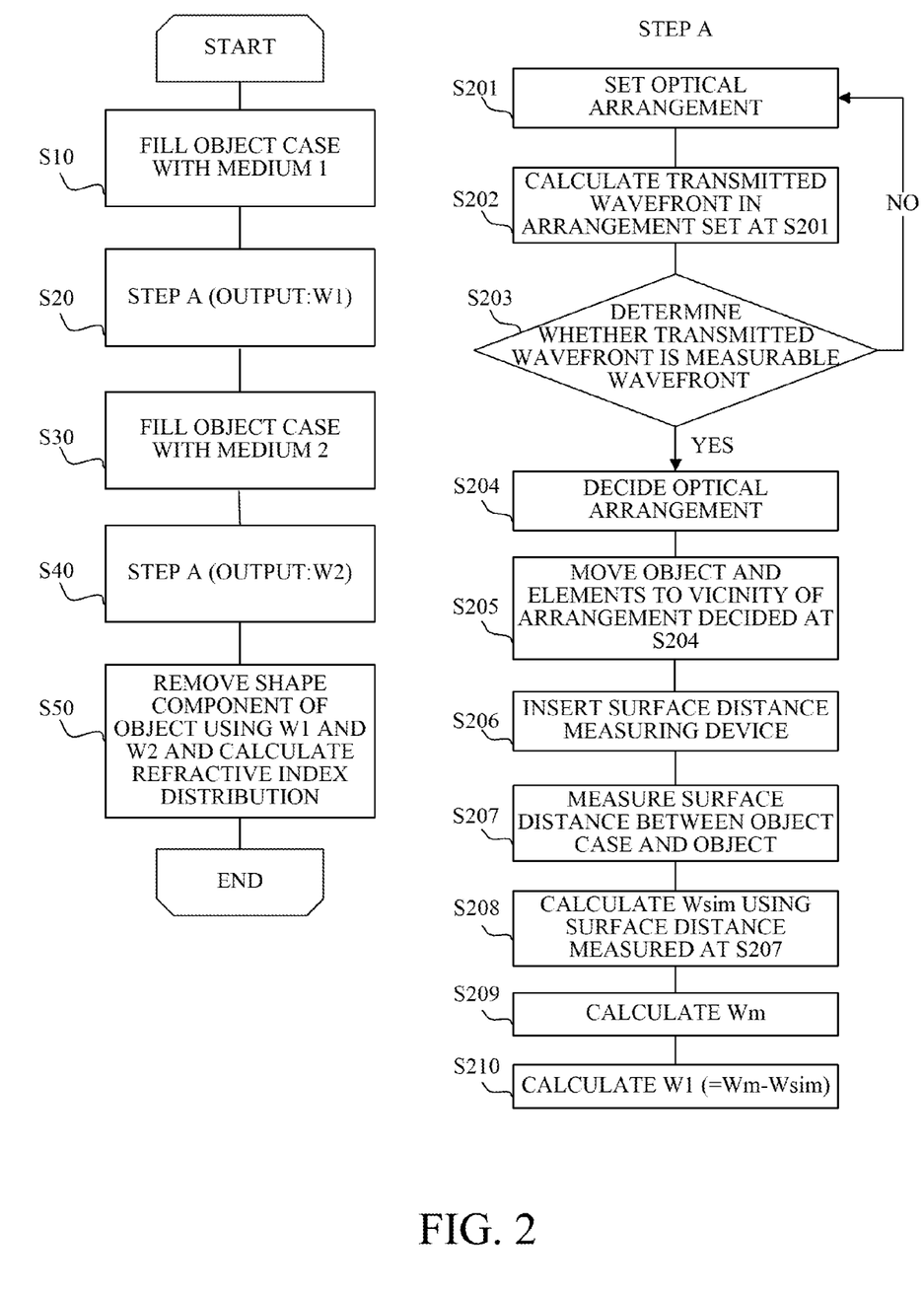
FIG. 2 is a flowchart showing an internal refractive index distribution calculating procedure in Embodiment 1.

FIG. 2 shows a procedure for calculating an internal refractive index distribution (hereinafter simply referred to as a "refractive index distribution") GI of the object 120 by using an image captured by the CCD 140. In the procedure, calculation processing is executed by a computing unit (calculating part) 160 shown in FIGS. 1A and 1B such as a microcomputer, according to a computer program.

First, as shown in FIG. 1A, the procedure fills an inside of the object case 121 with air, and places the object 120 therein (step S10). The air is shown as "MEDIUM 1" in FIG. 2.

Next, the procedure measures, according to step A which will be described later, a transmitted wavefront when the medium in the object case 121 is the air and then calculates a wavefront aberration W1 (Step S20). This step 20 corresponds to a first measuring step.

Step A will hereinafter be described. In this embodiment, a measurement result of the transmitted wavefront includes (a) the refractive index distribution of the object 120, (b) an influence of a shape of the object 120, (c) an influence of a shape error of the object 120 and (d) an offset generated by a measuring system. This embodiment calculates by simulation (b) the influence of the shape of the object 120 and (d) the offset generated by the measuring system, and then subtracts them from the measurement result of the transmitted wavefront. Step A is a process to calculate the remains, that is, (a) the refractive index distribution of the object 120 and (c) the influence of the shape error (shape component) of the object 120 as the wavefront aberration W1.

Step A includes the following ten steps. First, the procedure sets an optical arrangement that is an arrangement of the optical elements (the pinhole 110, the object case 121, the diffraction grating 130 and the CCD 140) and the object 120 (step S201).

Next, the procedure (calculation processing) calculates what transmitted wavefront is obtained on the CCD 140 in the optical arrangement set in step S201 (step S202). In this calculation, since the refractive index distribution of the object 120 is unknown, the transmitted wavefront is calculated by using an arbitrarily assumed refractive index distribution or an ideal (specific) refractive index distribution that is an unbiased distribution or an even distribution.

Next, the procedure determines whether or not the calculated transmitted wavefront is a measurable wavefront (step S203). In order to obtain the self-image of the diffraction grating 130 on the entire surface of the CCD 140 in the Talbot interferometer, the NA of a light flux reaching the CCD 140 should be suppressed to about 0.3 or less. If the NA of the light flux reaching the CCD 140 is larger than 0.3, if light fluxes passing through different portions of the object 120 overlap each other on the CCD 140, or if a size of the light flux on the CCD 140 is excessively large or excessively small, the procedure returns to step S201 to reset the optical arrangement. If determining that the calculated transmitted wavefront is a measurable wavefront, the procedure employs the optical arrangement set at that time as an optical arrangement to be used in the following measurement (step S204), and moves the object 120 and the respective optical elements to the vicinity of the employed (decided) optical arrangement along the rail 150 (step S205). The diffraction grating 130 and the CCD 140 are hereinafter collectively referred to as the "sensor".

Figure 3:
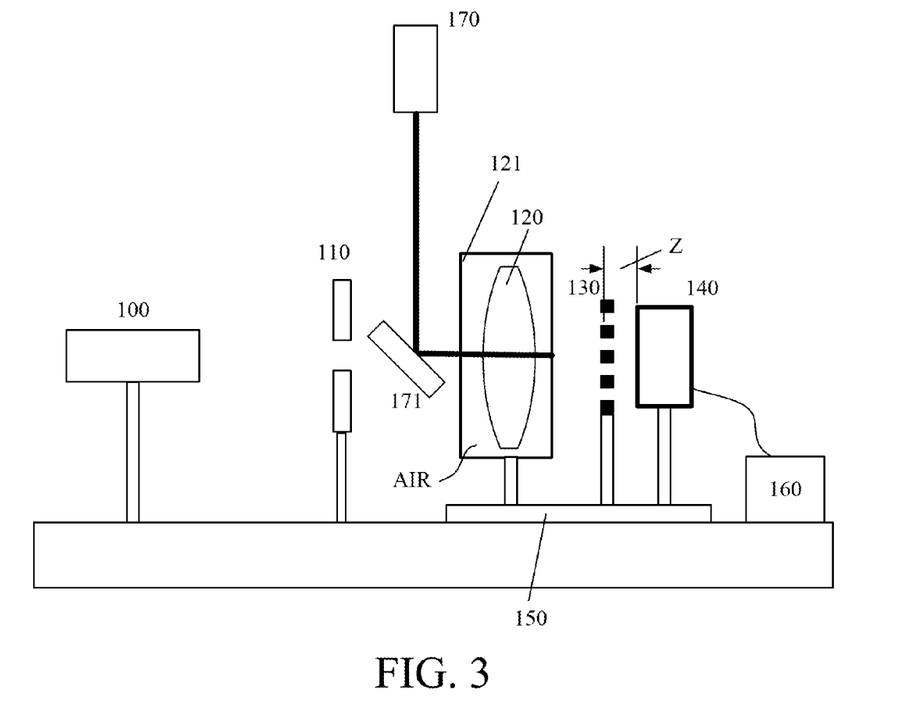
FIG. 3 shows a flowchart showing a subroutine performed at step S207 of Embodiment 1.

Subsequently, description will be made of a step (position measuring step) of measuring distances between surfaces of the object 120 and the optical elements, that is, arrangement positions of the object 120 and the optical elements with reference to FIG. 3. The distances between the surfaces of the object 120 and the optical elements are hereinafter referred to as the "surface distances", and the arrangement positions of the object 120 and the optical elements are hereinafter referred to as the "surface positions". This step uses a surface distance measuring device (position measuring part) 170 capable of measuring thicknesses of the object case 121 and the object 120 from an outside of the object case 121.

When measuring the surface distance between the optical elements, the procedure inserts the surface distance measuring device 170 into a measuring light flux between those optical elements (step S206). The measuring light flux is a light flux exiting from the pinhole 110 to reach the CCD 140 and including the reference light 102 shown in FIG. 1A. In a case where there is no space into which the surface distance measuring device 170 is inserted between the optical elements, a mirror 171 may be inserted in the measuring light flux between the optical elements as shown in FIG. 3 so as to place the surface distance measuring device 170 outside the measuring light flux. In this case, it is not necessary to move the surface distance measuring device 170.

Subsequently, the procedure measures the surface distance from a window glass of the object case 121 to the object 120 by using the surface distance measuring device 170 (step S207). In this measurement, further measurement may be made of a thickness of the window glass of the object case 121, the surface distance from the object case 121 to the diffraction grating 130 and the surface distance from the object case 121 to the CCD 140. Although FIG. 3 shows the case where the mirror 171 is inserted between the pinhole 110 and the object case 121, inserting the mirror 171 between the object case 121 and the diffraction grating 130 enables measurement of the surface distance from the pinhole 110 to the object case 121.

As the surface distance measuring device 170, for example, a device may be used which includes a low-coherence light source and a beam splitter that splits detecting light from the reference light, and which is capable of outputting an interference signal when an optical path length of the detecting light coincides with that of the reference light. In this case, even if plural optical elements such as the object case 121 and the object 120 exist on an optical path of the detecting light, changing the optical path length of the reference light enables measurement of the respective surface positions. Moreover, since the measured surface distance corresponds to an optical surface distance, that is, a distance in vacuum, a geometric surface distance is calculated by using a refractive index of a material or a medium between the surfaces.

Furthermore, as the surface distance measuring device 170, a device may be used which is capable of changing a wavelength of a built-in light source as disclosed in Japanese Patent Laid-Open No. 2001-099624. In this case, image capture with wavelength change (phase shift) enables separation of reflected light fluxes coming from the respective surfaces to specify the surface positions.

In addition, as the surface distance measuring device 170, a device may be used which includes a collective lens and a sensor for detecting a position of the collective lens as disclosed in Japanese Patent Laid-Open No. 10-325795. In this case, calculating a focus position of each optical element's surface on the basis of an interference intensity and detecting a movement distance of the collective lens enable measurement of respective surface distances.

Next, the procedure calculates a simulation wavefront (first reference transmitted wavefront) $W_{sim}$ for a case where an object (reference object) corresponding to the object 120 is assumed to have the specific (ideal) refractive index distribution by using information on the surface distance measured at step S207 (step S208). At this step, the procedure separately calculates, in an optical arrangement identical to that decided at step S204, that is, in a state where the object (reference object) and the optical elements are assumed to be arranged at same positions as those decided at step S204, a transmitted wavefront for a case where the refractive index distribution of the object is already-known. Such an object whose refractive index distribution is already-known is referred to as the "reference object". The reference object has a shape identical to that of the object 120. The already-known refractive index distribution may be a designed value or a measured value.

The simulation wavefront $W_{sim}$ can be regarded as a transmitted wavefront of the reference object placed in the air. The simulation wavefront $W_{sim}$ at a certain point (x,y) in the reference object is expressed by the following expressions (3):

$$W_{sim}(x,y) = OP_{sim}(x,y) - OP_{sim}(0,0)$$

$$OP_{sim}(x,y) = L1(x,y) + L2(x,y)N_1 + L3(x,y)Ng + L4(x,y)N_1 + L5(x,y) \quad (3)$$

Figure 4:
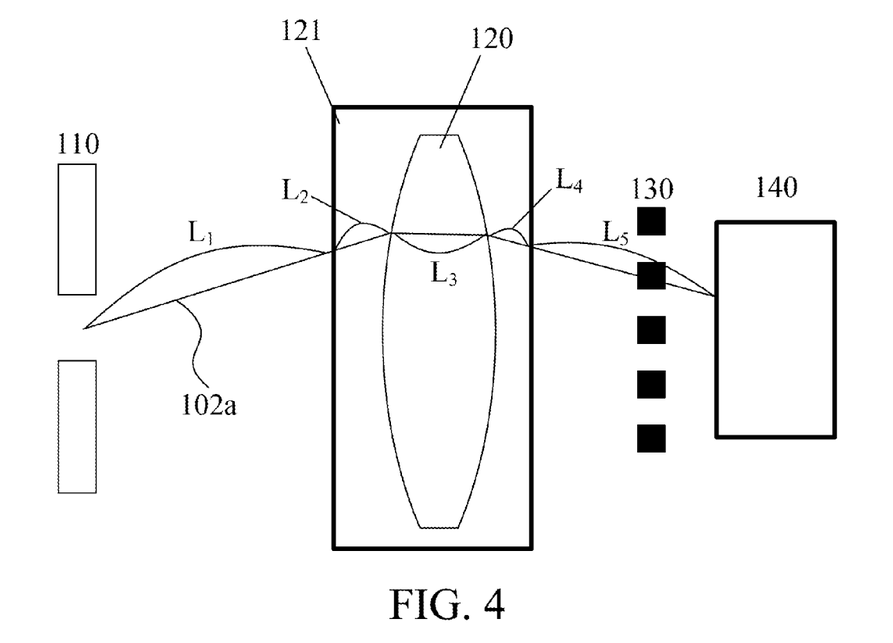
FIG. 4 shows an optical path in the refractive index distribution measuring apparatus of Embodiment 1.

In the above expressions, L1 to L5 represent geometric distances between the surfaces of the above-described elements (110, 121, 120, 130 and 140) along a light ray 102a shown in FIG. 4. In FIG. 4, the reference object is denoted by a same reference numeral 120 as that of the object. The light ray 102a schematically shows a light ray passing the certain point (x,y) in the reference object. N1 represents a refractive index of the air, and Ng represents the specific (ideal) refractive index of the object 120 (that is, the refractive index of the reference object). The above expressions ignore the thickness of the window glass (wall) of the object case 121 for simplification.

Next, the procedure measures a transmitted wavefront (first transmitted wavefront) $W_m$ in the state where the object 120 is soaked in the air in the Talbot interferometer shown in FIG. 1A (step S209). This step includes image capture for capturing an image of interference fringes by the CCD 140 and image restoration for restoring (or retrieving) the transmitted wavefront by a processing circuit (not shown). The image restoration of the transmitted wavefront (hereinafter referred to as the "wavefront retrieval") is executed by an FFT (fast Fourier transformation) method. The wavefront retrieval by the FFT method utilizes a property of aberration that disturbs a carrier fringe of the interference fringes to separate the carrier fringe from the aberration.

Specifically, the wavefront retrieval performs a two-dimensional FFT on the interference fringes to convert it into a frequency map. Next, the wavefront retrieval extracts part in the vicinity of the career frequency from the frequency map to perform coordinate transformation thereof such that the career frequency becomes a coordinate origin, and then performs iFFT (inverse fast Fourier transformation). This processing enables calculation of a phase term of a complex amplitude map, and a phase map thus obtained shows the transmitted wavefront.

The transmitted wavefront $W_m$ is expressed by using L1 to L5 in FIG. 4 as the following expressions (4).

$$W_m(x,y) = OP_m(x,y) - OP_m(0,0)$$

$$OP_m(x,y) = L1(x,y) + L2(x,y)N_1 + \{L3(x,y) + dL\}N(x,y) + \{L4(x,y) - dL\}N_1 + L5(x,y) \quad (4)$$

In this expression (4), N(x,y) represents a refractive index averaged in a direction of an optical path passing through a certain point whose coordinate is (x,y) in the object 120. dL represents a thickness error of the object 120 at the certain point (x,y).

The procedure calculates at the end of step A the wavefront aberration W1 corresponding to a difference between the simulation wavefront $W_{sim}$ obtained at step S208 and the transmitted wavefront $W_m$ obtained at step S209. The wavefront aberration W1(=$W_m$-$W_{sim}$) is expressed by the following expression (5):

$$W1 = W_m - W_{sim}$$
$$= L3(x,y)\{N(x,y) - Ng\} + dL(x,y)\{N(x,y) - N_1\} - dL(0,0)\{Ng - N_1\} \quad (5)$$

where Ng is assumed to be equal to a central refractive index N(0,0) of the object 120 to simplify the expression (5).

Next, as shown in FIG. 1B, the procedure fills the inside of the object case 121 with water, and places the object 120 therein. The water is shown as "MEDIUM 2" in FIG. 2. Then, the procedure measures, according to step A which has been described above, a transmitted wavefront when the medium in the object case 121 is the water, and calculates a wavefront aberration W2 by using the following expression (6) (Step S40):

$$W2 = W_m - W_{sim}$$
$$= L3(x,y)\{N(x,y) - Ng\} + dL(x,y)\{N(x,y) - N_2\} - dL(0,0)\{Ng - N_2\} \quad (6)$$

where $N_2$ represents the refractive index of the water. This step 40 corresponds to a second measuring step. $W_{sim}$ represents a simulation wavefront (second reference transmitted wavefront) of the above-described reference object in a state where the reference object and the optical elements are assumed to be arranged in the water at same positions as those decided at step S204.

Next, the procedure removes the thickness error (shape component) dL of the object 120 from the wavefront aberration W1 and the wavefront aberration W2 by the following expression (7), and calculates the refractive index distribution N(x,y) of the object 120 from which the thickness error dL is removed (step S50). Thus, the measurement and calculation of the refractive index distribution are completed. In the calculation of the refractive index distribution N(x,y), the procedure uses an approximation expression shown by the following expression (8):

$$N(x,y) = Ng + \frac{1}{L3(x,y)} \times \frac{(Ng - N_1)W2 - (Ng - N_2)W1}{N_2 - N_1} \quad (7)$$

$$\{N(x,y) - Ng\}dL(x,y) \approx 0 \quad (8)$$

Although this embodiment described the procedure which measures the surface distance after filling the object case 121 with the water, the procedure is not limited thereto. For example, a procedure may be employed which places the object in the object case to measure the surface distance, and then fills the object case with the water.

Using the Talbot interferometer as the refractive index measuring apparatus as this embodiment enables measurement of a large aberration caused due to a refractive index difference between the object and the medium. The Talbot interferometer is one of lateral shearing interferometers, which measures a difference between a transmitted wavefront from the object and a laterally shifted (sheared) transmitted wavefront as interference fringes. Therefore, it can be said that the shearing interferometer is a measurement apparatus which measures an amount corresponding to a gradient (inclination) of a wavefront shape of a transmitted wavefront. A lateral shift amount of the transmitted wavefront is referred to as a "shear amount". Reducing the shear amount enables measurement of a large transmitted wavefront aberration as a small aberration (shear wavefront) that does not cause dense interference fringes.

Generally in the shearing interferometer, the shear wavefront is buried in noises when the shear amount is too small, and thereby measurement accuracy is decreased. Thus, the shear amount is preferably set to about 3 to 5% of a diameter of a pupil. However, in this embodiment, in order to measure a transmitted wavefront with a large aberration as a small shear wavefront, it is desirable to reduce the shear amount to 1.5% or less, more desirably to about 0.4 to 0.9%.

The shear amount "shear" is defined by the following expression (9) using the Talbot distance Z and a diameter D of interference fringe data on the CCD 140:

$$\text{shear} = \frac{\lambda Z}{dD} \qquad (9)$$

The above expression (9) can be expressed as the following expression (10) by using the expression (2) and a diameter $D_0$ of a light flux on the diffraction grating 130:

$$\text{shear} = \frac{md}{D_0} \qquad (10)$$

The above expression (10) shows that the shear amount is proportional to the grating pitch of the diffraction grating 130. The grating pitch of the diffraction grating 130 influences the Talbot distance Z as understood from expression (2), so that it is necessary to decide the grating pitch with consideration of interferences between the constituent elements of the measuring apparatus. For example, when m is 1 and $D_0$ is about 10 to 20 mm, the grating pitch is desirable to be about 40 to 180 µm.

As described above, this embodiment measures the first transmitted wavefront of the object by causing the reference light to enter the object placed in the air having a refractive index lower than that of the object by 0.01 or more, and measures the second transmitted wavefront of the object by causing the reference light to enter the object placed in the water having a refractive index lower than that of the object by 0.01 or more and different from that of the air by 0.01 or more. Moreover, this embodiment measures the placement positions of the object in the air and in the water. Furthermore, this embodiment obtains, by calculation, first and second reference transmitted wavefronts of the reference object having the specific refractive index distribution to be placed at the same positions as those when the measurements of the first and second transmitted wavefronts are made in the air and the water. In addition, this embodiment calculates the difference between the measured and reference first transmitted wavefronts and the difference between the measured and reference second transmitted wavefronts to calculate on the basis of those differences the refractive index distribution of the object from which the shape component of the object is removed.

Accordingly, this embodiment can highly accurately measure the internal refractive index distribution of the object by using the media having the refractive indices lower than that of the object, even when the refractive index of the object is high, without requiring highly accurate positioning of the object.

Although this embodiment described the case where the two media are air and water, the two media may be other media having refractive indices different from each other by 0.01 or more. As the two media, same materials may be used which are provided with different refractive indices by a difference of their temperatures.

Moreover, although this embodiment described the case where the Talbot interferometer is used, other lateral shearing interferometers, radial shearing interferometers and other shearing interferometers may be used.

[Embodiment 2]

Figure 5:
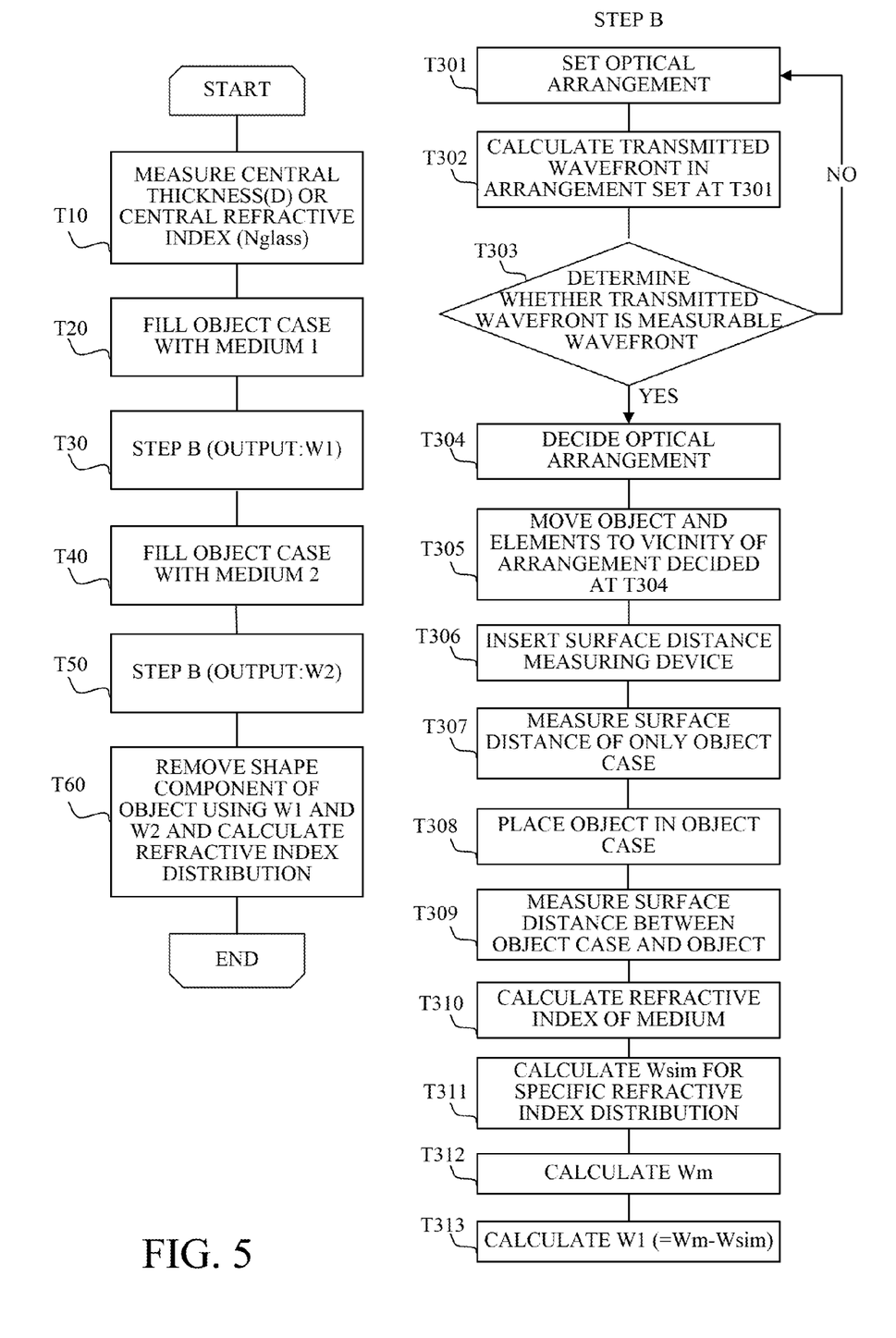
FIG. 5 is a flowchart showing an internal refractive index distribution calculating procedure in Embodiment 2 of the present invention.

A second embodiment (Embodiment 2) of the present invention will describe a case of simultaneously measuring a refractive index of a medium to reflect it into calculation of the refractive index distribution of the object. A flowchart of FIG. 5 shows a procedure for calculating the refractive index distribution in this embodiment. This embodiment will describe differences from the procedure in Embodiment 1 (FIG. 2). The procedure shown in FIG. 5 is different in steps T10 and T305 to T311 from that shown in FIG. 2.

In this embodiment, the procedure first measures a thickness (central thickness) D of a center of the object 120 or a central refractive index $N_{glass}$ that is a refractive index averaged in a thickness direction at the center of the object (step T10).

Thereafter, at steps T20 to T60, the procedure performs step B to calculate a wavefront aberration W1 in a case where a medium in the object case 121 is air (first medium, MEDIUM 1) and a wavefront aberration W2 in a case where the medium is water (second medium, MEDIUM 2).

In step B, the procedure first performs same processes as those at steps S201 to S204 in Embodiment 1 (steps T301 to T304).

Thereafter, the procedure places at step T305 an optical element to the vicinity of a position in an optical arrangement decided at step T304 (corresponding to step S204 in FIG. 2). At this step, in order to measure a surface distance of only the object case 121 at a subsequent step, the procedure keeps the object 120 outside the object case 121.

Next, the procedure inserts a surface distance measuring device into the apparatus as at step S206 (step T306), and then measures an optical surface distance $Z_0$ of only the object case 121 (step T307). Thereafter, the procedure places the object 120 inside the object case 121 (step T308). Then, the procedure measures an optical surface distance between the object case 121 and the object 120 by using the inserted surface distance measuring device (step T309). In the measurement, a front side optical surface distance from a front side window glass of the object case 121 to the object 120 is defined as $Z_1$, and a rear side optical surface distance from a rear side window glass of the object case 121 to the object 120 is defined as $Z_3$. An optical thickness of the object 120 is defined as $Z_2$.

Next, the procedure calculates a refractive index of the medium based on the optical surface distances including the optical thickness $Z_2$ of the object 120 measured at step T307 and step T309 (step T310).

In a case where the central thickness D of the object 120 is already-known at step T10, the procedure calculates the refractive index of the medium (first medium) according to the following expression (11) where $N_1$ represents a refractive index of the first medium:

$$N_1 = \frac{Z_0 - Z_1 - Z_3}{D} \qquad (11)$$

Moreover, in a case where the central refractive index $N_{glass}$ of the object 120 is already-known at step T10, the procedure calculates a refractive index of the first medium according to the following expression (12):

$$N_1 = \frac{Z_0 - Z_1 - Z_3}{Z_2} N_{glass} \quad (12)$$

Next, the procedure calculates a simulation wavefront $W_{sim}$ for a case where the object 120 has an ideal refractive index distribution (specific refractive index distribution) by using information on the optical surface distances measured at step T309 and the refractive index measured at step T310 (step T311). That is, the procedure calculates the simulation wavefront $W_{sim}$ by using the refractive index calculated at step T310 as the refractive index $N_1$ of the first medium in the expression (3), an expression used in this calculation being similar to that in Embodiment 1. The above description was made of the process for calculating the refractive index $N_1$ of the first medium. The process is also applied for calculating a refractive index $N_2$ of a second medium. The process for calculating the refractive index may be performed on at least one of the first and second media. Furthermore, the refractive index of the medium may be calculated on the basis of at least one of the thickness and the refractive index of the object.

The procedure calculates at the end of step B a transmitted wavefront of the object 120 (step T312), and then a difference between the measured and calculated transmitted wavefronts (step T313), as at steps S209 and S210 in Embodiment 1.

This embodiment can highly accurately measure the refractive index of the object 120 even when the refractive index of the media is unknown.

[Embodiment 3]

Figure 6:
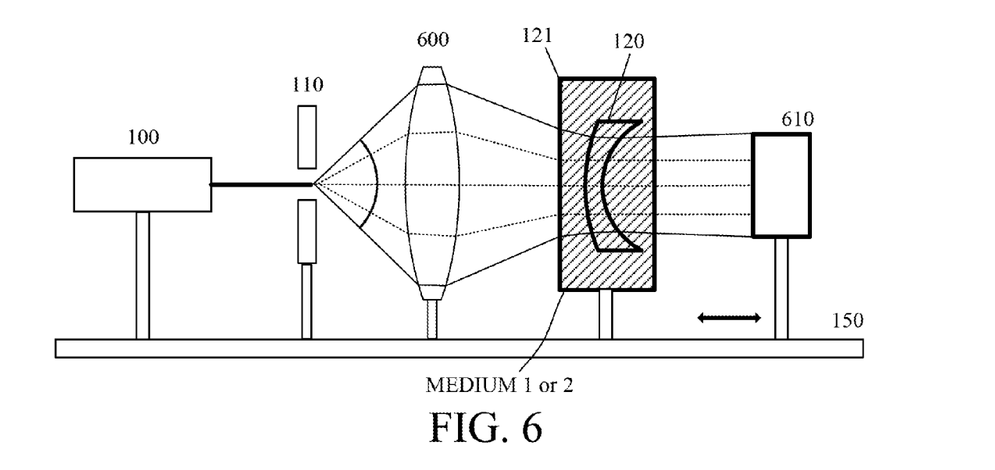
FIG. 6 schematically shows a configuration of a refractive index distribution measuring apparatus that is Embodiment 3 of the present invention.

A third embodiment (Embodiment 3) of the present invention will describe a case where an object 120 has a negative optical power (an optical power is an inverse of a focal length) and a refractive index measuring apparatus other than the shearing interferometer is used. FIG. 6 schematically shows a configuration of the refractive index measuring apparatus of this embodiment.

Figure 7:
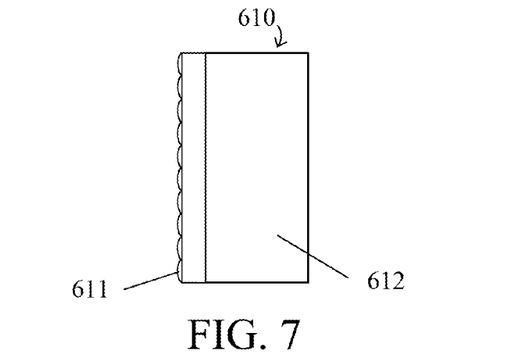
FIG. 7 schematically shows a Shack-Hartmann sensor being used in Embodiment 3.

A pinhole 110 generates light (reference light) having an ideal spherical wave using laser light emitted from a laser light source 100. The light is converted into convergent light by an illumination system 600. The convergent light passes through the object 120 that is a meniscus lens, and a transmitted wavefront thereof is measured by a Shack-Hartmann sensor 610 that is a wavefront measuring sensor. The Shack-Hartmann sensor 610 is constituted by a lens array 611 and a CCD 612 as shown in FIG. 7.

Moving the object 120 in an optical axis direction along a rail 150 enables a light flux entering the object 120 to change into any of a divergent light flux, a collimated light flux and a convergent light flux. This makes it possible to adjust an NA of the light flux entering the Shack-Hartmann sensor 610.

The Shack-Hartmann sensor 610 requires a more strict management of the NA of the light flux entering thereinto as compared with the Talbot interferometer. The Shack-Hartmann sensor 610 has a structure that collects the light flux entering the lens array 611 on the CCD 612. An inclination of the transmitted wavefront entering the lens array 611 causes a displacement of a light collecting point. The Shack-Hartmann sensor 610 can measure a wavefront having a large aberration since it is capable of measuring such a wavefront by converting the inclination of the transmitted wavefront into the displacement of the light collecting point.

A procedure (method) for calculating an internal refractive index distribution of the object 120 in this embodiment is same as that in Embodiment 1, and therefore description thereof is omitted.

The measuring apparatus being used in this embodiment only has to be capable of measuring an amount corresponding to the gradient of the wavefront shape of the transmitted wavefront or the inclination of the light flux (light ray) so as to detect the gradient or the inclination as a physical amount even when the transmitted wavefront has a large aberration. Therefore, measuring apparatuses using a Hartmann method or a Ronchi test may also be used.

[Embodiment 4]

It is possible to feed back the measurement result obtained by the refractive index distribution measuring apparatus (or the refractive index distribution measuring method) described in any one of Embodiments 1 to 3 to a manufacturing method of an optical element such as a lens.

Figure 8:
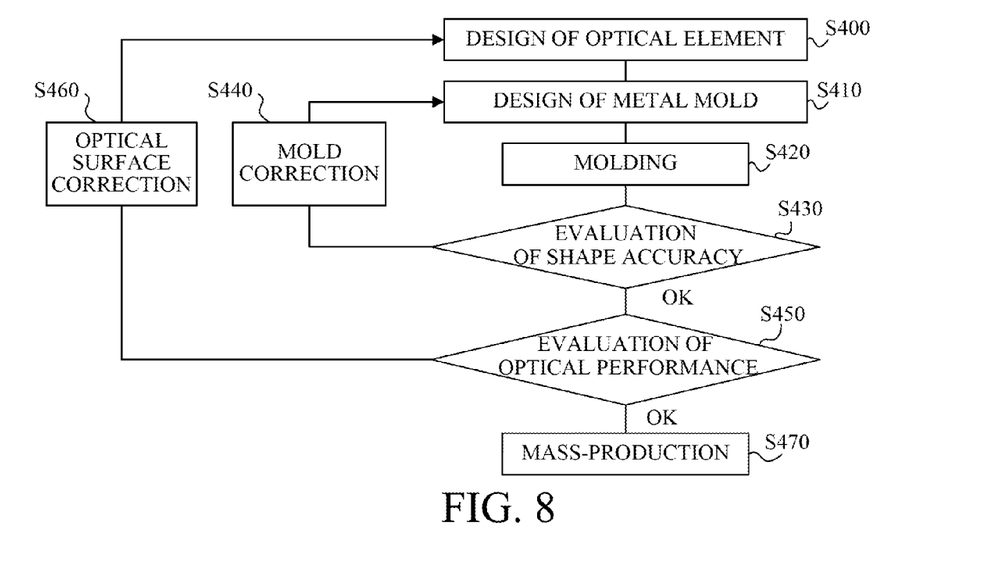
FIG. 8 shows a manufacturing method of an optical element using any one of Embodiments 1 to 3.

FIG. 8 shows an example of the manufacturing method of the optical element using molding.

In FIG. 8, Step S400 is a step of designing the optical element where a designer designs the optical element by using optical design software.

Step S410 is a step of designing and processing a metal mold for molding the optical element on the basis of the optical element design made at step S400.

Step S420 is a step of molding the optical element by using the metal mold processed at step S410.

Step S430 is a step of measuring a shape of the optical element molded at step S420 and evaluating accuracy thereof. If the shape evaluated at step S430 does not satisfy required accuracy, the manufacturing method calculates at step S440 a correction amount of the metal mold, and then reprocesses at step S410 the metal mold by using the correction amount.

Step S450 is a step of evaluating optical performance of the optical element satisfying the required accuracy in shape at step S430. The manufacturing method executes at step S450 the refractive index distribution calculation processing described in FIG. 2 or FIG. 5, and evaluates the optical performance of the optical element by using the calculation result. If the optical performance evaluated at step S450 does not satisfy required specifications, the manufacturing method calculates at step S460 correction amounts of optical surfaces of the optical element, and redesigns at step S400 the optical element by using the correction amounts.

Step S470 is a step of mass-producing the optical element under optical element manufacturing conditions that can achieve the required optical performance at step S450.

The optical element manufacturing method of this embodiment enables accurate measurement of the internal refractive index distribution of the optical element, which makes it possible to mass-produce the optical elements accurately by molding even when the optical element is formed of a high refractive index glass material.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-277496, filed on Dec. 7, 2009, which is hereby incorporated by reference herein in its entirety.

What is claimed is:

1. A refractive index distribution measuring method comprising:

a first measuring step of placing an object in a first medium having a first refractive index lower than a refractive index of the object, and of causing reference light to enter the object to measure a first transmitted wavefront of the object;

a second measuring step of placing the object in a second medium having a second refractive index lower than the refractive index of the object and different from the first refractive index, and of causing the reference light to enter the object to measure a second transmitted wavefront of the object;

a position measuring step of measuring a first placement position where the object is placed in the first medium and a second placement position where the object is placed in the second medium; and a calculating step of calculating an internal refractive index distribution of the object using the measured first and second transmitted wavefronts, wherein the calculating step calculates the internal refractive index distribution from which a shape component of the object is removed using (a) the measured results first and second transmitted wavefronts, (b) a first reference transmitted wavefront of a reference object to be placed in the first medium at a position identical to the first placement position and (c) a second reference transmitted wavefront of the reference object to be placed in the second medium at a position identical to the second placement position, the reference object having a shape identical to that of the object and a specific internal refractive index distribution.

2. A refractive index distribution measuring method according to claim 1, wherein the calculating step calculates at least one of the first refractive index or the second refractive index based on at least one of a thickness of the object or the refractive index of the object.

3. A refractive index distribution measuring method according to claim 1, wherein:

the first measuring step measures an amount corresponding to a gradient of a wavefront shape of the first transmitted wavefront, and the second measuring step measures an amount corresponding to a gradient of a wavefront shape of the second transmitted wavefront.

4. A refractive index distribution measuring method according to claim 1, wherein the first refractive index and the second refractive index have a difference of 0.01 or more.

5. A manufacturing method of an optical element, the method comprising:

a molding step of molding the optical element; and an evaluating step of evaluating the optical element, wherein the evaluating step measures an internal refractive index distribution of the optical element using a refractive index distribution measuring method comprising:

a first measuring step of placing the optical element in a first medium having a first refractive index lower than a refractive index of the optical element, and of causing reference light to enter the optical element to measure a first transmitted wavefront of the optical element;

a second measuring step of placing the optical element in a second medium having a second refractive index lower than the refractive index of the optical element and different from the first refractive index, and of causing the reference light to enter the optical element to measure a second transmitted wavefront of the optical element;

a position measuring step of measuring a first placement position where the optical element is placed in the first medium and a second placement position where the optical element is placed in the second medium; and a calculating step of calculating the internal refractive index distribution of the optical element using the measured results of the first and second transmitted wavefronts, wherein the calculating step calculates the internal refractive index distribution from which a shape component of the object is removed using (a) the measured the first and second transmitted wavefronts, (b) a first reference transmitted wavefront of a reference object to be placed in the first medium at a position identical to the first placement position, and (c) a second reference transmitted wavefront of the reference object to be placed in the second medium at a position identical to the second placement position, the reference object having a shape identical to that of the optical element and a specific internal refractive index distribution.

6. A refractive index distribution measurement apparatus comprising:

a transmitted wavefront measuring device comprising a first light source, a pinhole, and a sensor, wherein the transmitted wavefront measuring device (a) causes reference light to enter an object, which is placed in a first medium having a first refractive index lower than a refractive index of the object, to measure a first transmitted wavefront of the object, and (b) cause the reference light to enter the object, which is placed in a second medium having a second refractive index lower than the refractive index of the object and different from the first refractive index, to measure a second transmitted wavefront of the object;

a position measuring device comprising a second light source and a splitter, wherein the position measuring device measures a first placement position where the object is placed in the first medium and a second placement position where the object is placed in the second medium; and a microcomputer programmed to calculate an internal refractive index distribution of the object using the measured first and second transmitted wavefronts, wherein the microcomputer calculates the internal refractive index distribution from which a shape component of the object is removed using (a) the measured first and second transmitted wavefronts, (b) a first reference transmitted wavefront of a reference object to be placed in the first medium at a position identical to the first placement position and (c) a second reference transmitted wavefront of the reference object to be placed in the second medium at a position identical to the second placement position, the reference object having a shape identical to that of the object and a specific internal refractive index distribution.

7. A refractive index distribution measuring method comprising:

a first measuring step of placing an object in a first medium having a first refractive index lower than a refractive index of the object, and of causing reference light to enter the object to measure a first transmitted wavefront of the object;

a second measuring step of placing the object in a second medium having a second refractive index lower than the refractive index of the object and different from the first refractive index, and of causing the reference light to enter the object to measure a second transmitted wavefront of the object;

a position measuring step of measuring a first placement position where the object is placed in the first medium and a second placement position where the object is placed in the second medium; and a calculating step of calculating a refractive index distribution of the object using the measured first and second transmitted wavefronts, wherein the calculating step (a) calculates a first wavefront aberration, which is a difference between the measured first transmitted wavefront and a transmitted wavefront of a reference object having a shape identical to the object and a specific refractive index distribution when the reference object is placed at a position identical to the measured first placement position, (b) calculates a second wavefront aberration, which is a difference between the measured second transmitted wavefront and a transmitted wavefront of the reference object when the reference object is placed at a position identical to the measured second placement position, and (c) calculates a refractive index distribution of the object with a removal of a shape component of the object based on the calculated first and second wavefront aberrations.

8. A refractive index distribution measurement apparatus comprising:

a transmitted wavefront measuring device comprising a first light source, a pinhole, and a sensor, wherein the transmitted wavefront measuring device (a) causes reference light to enter an object, which is placed in a first medium having a first refractive index lower than a refractive index of the object, to measure a first transmitted wavefront of the object, and (b) causes the reference light to enter the object, which is placed in a second medium having a second refractive index lower than the refractive index of the object and different from the first refractive index, to measure a second transmitted wavefront of the object;

a position measuring device comprising a second light source and a splitter, wherein the position measuring device measures a first placement position where the object is placed in the first medium and a second placement position where the object is placed in the second medium; and a microcomputer programmed to calculate a refractive index distribution of the object using the measured first and second transmitted wavefronts, wherein the microcomputer (a) calculates a first wavefront aberration, which is a difference between the measured first transmitted wavefront and a transmitted wavefront of a reference object having a shape identical to the object and a specific refractive index distribution when the reference object is placed at a position identical to the measured first placement position, (b) calculates a second wavefront aberration, which is a difference between the measured second transmitted wavefront and a transmitted wavefront of the reference object when the reference object is placed at a position identical to the measured second placement position, and (c) calculates a refractive index distribution of the object with a removal of a shape component of the object based on the calculated first and second wavefront aberrations.

\* \* \* \* \*